(12) United States Patent
Potter

(10) Patent No.: US 6,601,860 B2
(45) Date of Patent: Aug. 5, 2003

(54) WAGON FOR USE IN A HOSPITAL

(76) Inventor: Angie Potter, 9372 Sonora, Brentwood, MO (US) 63144

( * ) Notice: Subject to any disclaimer, the term of this patent is extended or adjusted under 35 U.S.C. 154(b) by 18 days.

(21) Appl. No.: 10/025,734

(22) Filed: Dec. 19, 2001

(65) Prior Publication Data

US 2002/0101046 A1 Aug. 1, 2002

Related U.S. Application Data

(63) Continuation of application No. 09/546,088, filed on Apr. 10, 2000, now abandoned.

(51) Int. Cl.$^7$ ................................................. B62B 3/02
(52) U.S. Cl. ................................ 280/47.34; 280/47.35; 280/87.01; 248/129; 248/125.8
(58) Field of Search ......................... 280/47.34, 47.35, 280/87.01; 297/DIG. 4; 604/80, 246; 312/249.8, 249.11, 249.12, 249.13; 248/129, 125.8, 121, 122.1, 125.1, 145.6

(56) References Cited

U.S. PATENT DOCUMENTS

| | | | |
|---|---|---|---|
| 4,431,206 A | 2/1984 | Pryor | |
| 4,511,157 A | 4/1985 | Wilt, Jr. | |
| 4,511,158 A | 4/1985 | Varga et al. | |
| 4,572,536 A | 2/1986 | Doughty | |
| 4,600,209 A | 7/1986 | Kerr, Jr. | |
| 4,725,027 A | 2/1988 | Bekanich | |
| 4,729,576 A | 3/1988 | Roach | |
| 4,767,131 A | 8/1988 | Springer et al. | |
| 4,840,391 A | 6/1989 | Schneider | |
| 4,969,768 A | 11/1990 | Young | |
| 5,009,442 A | 4/1991 | Schneider | |
| 5,083,807 A | 1/1992 | Bobb et al. | |
| 5,094,418 A | 3/1992 | McBarnes, Jr. et al. | |
| 5,135,191 A | * 8/1992 | Schmuhl ................... | 248/125.1 |
| 5,149,036 A | 9/1992 | Sheehan | |
| 5,172,927 A | 12/1992 | Bobb et al. | |
| 5,187,824 A | 2/1993 | Stryker | |
| 5,219,139 A | 6/1993 | Hertzler et al. | |
| 5,236,213 A | 8/1993 | Trickett | |
| 5,288,093 A | 2/1994 | Gross | |
| 5,292,094 A | * 3/1994 | VanKuiken ............... | 248/125.1 |
| 5,319,816 A | 6/1994 | Ruehl | |
| 5,366,191 A | 11/1994 | Bekanich | |
| 5,374,074 A | 12/1994 | Smith | |
| 5,407,163 A | 4/1995 | Kramer et al. | |
| 5,421,548 A | 6/1995 | Bennett et al. | |
| 5,479,953 A | 1/1996 | Pasulka | |
| 5,513,406 A | 5/1996 | Foster et al. | |
| 5,551,105 A | 9/1996 | Short | |
| 5,556,065 A | * 9/1996 | Wadley ....................... | 248/129 |
| 5,556,118 A | * 9/1996 | Kern et al. .............. | 280/47.16 |
| 5,704,577 A | 1/1998 | Gordon | |
| 5,857,685 A | * 1/1999 | Phillips et al. .............. | 248/129 |
| 6,022,088 A | * 2/2000 | Metzler ...................... | 312/209 |
| 6,213,435 B1 | * 4/2001 | Minet ...................... | 248/125.8 |
| 6,231,016 B1 | * 5/2001 | Slone ...................... | 248/125.8 |
| 6,260,566 B1 | * 7/2001 | LaFave et al. ........... | 135/88.01 |
| 6,446,981 B1 | * 9/2002 | Wise et al. ................ | 280/7.17 |

OTHER PUBLICATIONS

Photograph of wagons used in Colorado (side view).
Photograph of wagons used in Colorado (front and rear view).
Photograph of wagons used in Colorado (rear view).

* cited by examiner

*Primary Examiner*—Brian L. Johnson
*Assistant Examiner*—J. Allen Shriver
(74) *Attorney, Agent, or Firm*—Senniger, Powers, Leavitt & Roedel

(57) ABSTRACT

A device for transporting children in a medical care facility is provided. The device includes a wagon carrying a pole inboard of the wheels. The pole is received in a holder whereby the wagon solely carries and supports the pole. The wagon includes a guard rail surrounding a wagon bed forming a passenger compartment with an upwardly opening top. The front wheels are independently pivotable for steering and stabilizing the wagon.

15 Claims, 4 Drawing Sheets

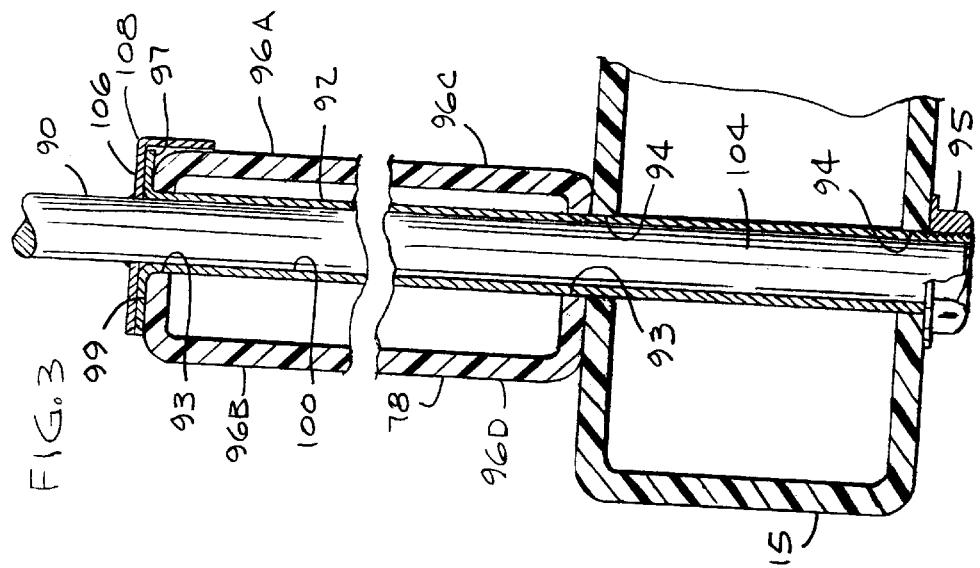
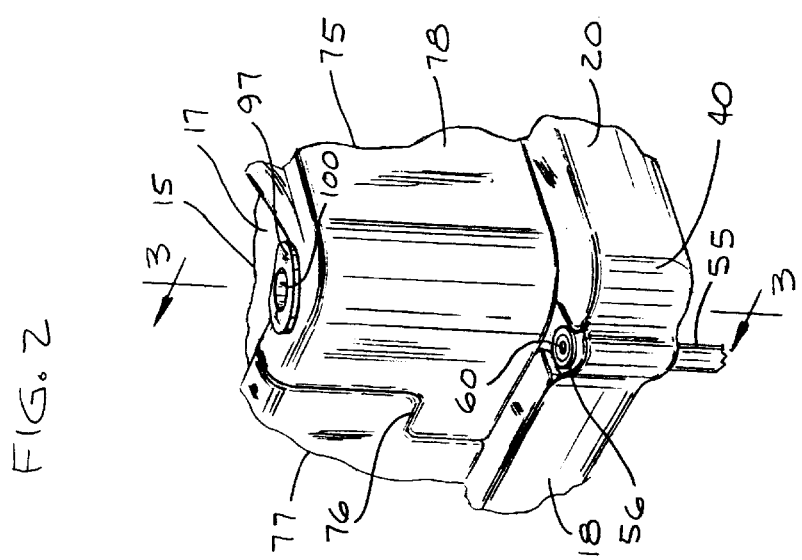

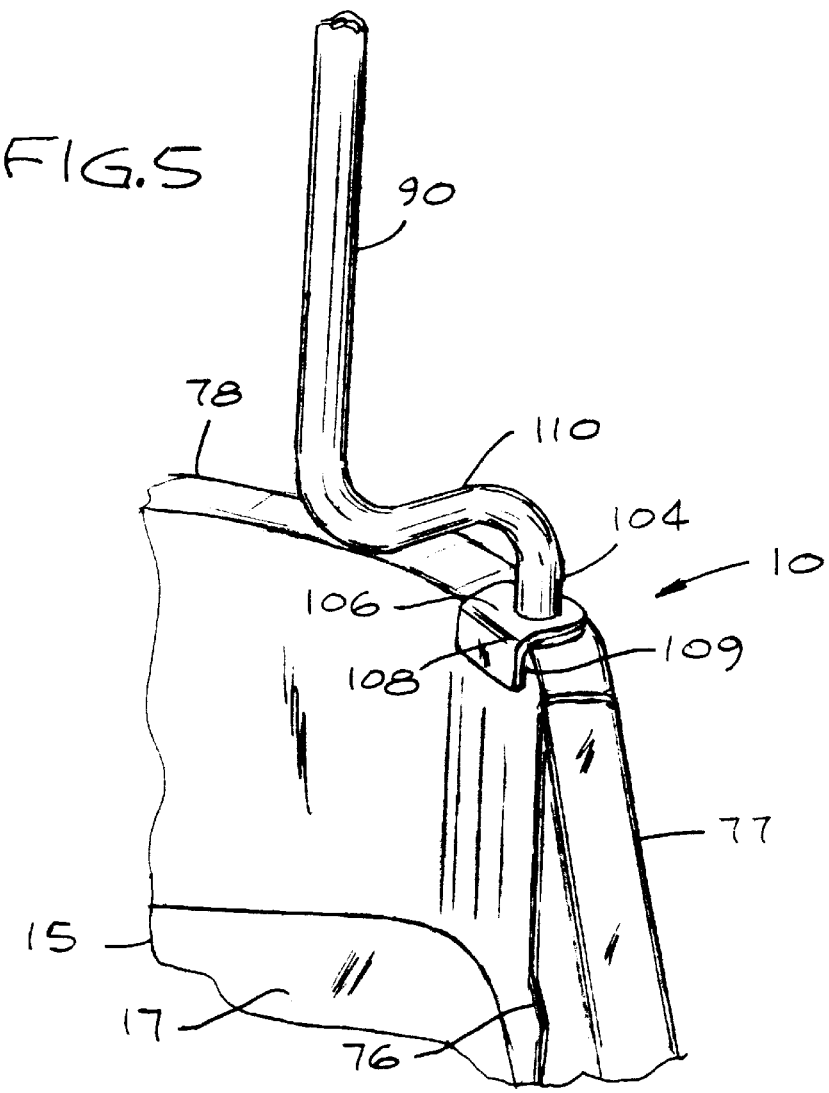

WAGON FOR USE IN A HOSPITAL

CROSS REFERENCE TO RELATED APPLICATIONS

The present application is a continuation of U.S. patent application Ser. No. 09/546,088 filed on Apr. 10, 2000, now abandoned.

BACKGROUND OF THE INVENTION

Children are cared for and provided medical treatment, including surgery, in medical care facilities such as hospitals and surgery centers. Stays in such facilities can be intimidating and cause much apprehension in young patients, despite the best efforts of a caring staff. Such apprehension can be the result of unfamiliar surroundings and equipment as well as unfamiliar ways of doing things and sometimes painful medical treatments. Further, unhappiness can result simply from being not being able to move freely about the facility.

During stays in treatment facilities, children are oftentimes immobile either because they are attached to medical devices like intravenous injection devices (I.V.'s), or their illness. The assisted movement of the child about the facility can help eliminate the feeling of immobility to make the child happier. However, the staff is generally not available for taking children for trips simply for fun. When a parent is visiting, they could move the child around to provide fun and mobility. To date though, the transport devices have presented obstacles for parents, generally the same obstacles the staff encounters when they transport the child for treatment. As discussed more in detail below, there are typically two transport devices used in care facilities, wheelchairs and wagons. Many children cannot be transported in wheelchairs because they cannot sit upright either because of age or illness. Further, the transport of an infusion pump, the preferred I.V. for children, on a wheel chair is difficult and poses safety concerns when attached to a pole attached to the wheelchair. If the I.V. is not attached to the wheelchair, two or more people would be required to move the child, wheelchair and I.V. around and two people may not be available when needed. In addition, a ride in a wheelchair is not generally viewed by a child as much fun. Wagons have been used instead of wheelchairs to provide an environment of fun for the child. Even though wagons can be effectively used to transport children who cannot sit upright and provide added fun by alleviating the feeling of immobility, they too have posed problems, such as safety and user convenience, as discussed below.

Children will also require movement about the facility by the staff to provide medical treatment. The children will realize or soon learn that a trip with staff within the facility usually results in a treatment which many times is unpleasant. Oftentimes, the contemplation of a treatment is worse than the treatment itself. Many of these children have little understanding of the treatments they will receive or the purpose of the treatment, except in the most general terms, adding to the anxiety and apprehension of being in an unfamiliar environment. The facility's staff works to reduce the apprehension and anxiety through the use of many mechanisms Such mechanisms include providing an atmosphere of fun to distract a child from thinking about what may occur particularly at the end of a trip in the facility. A ride in a wagon can provide such an atmosphere of fun.

During movement about, children will oftentimes be required to travel while connected to an I.V. or other medical device. Being connected to such a medical device also makes a child immobile unless they are being helped. Drip type I.V. bags have not been preferred for use with children since the flow rate can be easily changed by the child and they are not very accurate in flow rate at the lower flow rates of medicine used for children both of which create safety concerns. Typically, children are connected to an infusion pump for intravenous injection to more accurately regulate the injection of medicines or the like than can be accomplished with the drip type I.V. bags and because infusion pumps are relatively tamper resistant. Even though infusion pumps are preferred, they are typically large and heavy, presenting safety concerns should one fall on a child if not properly secured.

As discussed above, movement of a child about a care facility is typically accomplished using a wheelchair or a wagon. The use of a wheelchair presents problems. Wheelchairs may require two staff members, one to push while another staff member walks along with the I.V. on a wheeled pole. The use of wheelchairs and attendance by two staff members can be intimidating and cause additional apprehension in children. Devices have been provided to attach the I.V. device to the wheelchair to allow operation of the wheelchair by only one staff member. Although providing an improvement in efficiency such an arrangement can still cause apprehension and present safety and convenience issues. Because of the size and weight of an infusion pump, they are difficult to mount to a wheelchair. They either project over the seat area and patient or outwardly past the wheels. Projecting over the seat area makes entry, exit and sitting difficult. This position of the infusion pump also provides a safety concern since the device is positioned over the upper body of the child and should the device fall, a major injury could result. When projecting out over the wheels, there is a risk it will hit something or cause an empty chair to tip. Further, many children do not have the capacity to be upright in a wheel chair for various reasons, e.g., they may be too young or may not have sufficient muscle strength to sit upright making the use of a wheel chair not acceptable for such children. If a wheeled dolly is used to help support the pole and prevent wheelchair tipping, it too may hit an object causing damage. The wheels are also noisy and many times do not properly steer both of which can cause apprehension and make operation difficult. More importantly, the dolly wheels may catch causing the I.V. device to fall which in turn may painfully pull out the catheters and cause excessive bleeding.

Recently, wagons have been used for transport to provide a fun environment and allow children who cannot sit upright to be transported, but present their own problems. One such wagon is disclosed in U.S. Pat. No. 5,292,094. The wagon has a bracket for attaching an I.V. pole with a wheeled dolly attached to its bottom for rolling on the floor. The pole is attached to the side of the wagon adjacent a rear wheel with a clamp and two bolts. The dolly rests on the floor to provide vertical support for the pole and medical device(s) thereon. The problems with the use of a wheeled dolly are discussed above. For transport, a child is placed in the wagon and their I. V. pole and platform are then secured to the wagon via a clamp and bolt arrangement. Such an attachment is cumbersome and time consuming, potentially adding to the child's apprehension. At the end of the trip, the pole must also be similarly released from the wagon by loosening the two bolts, all potentially additionally adding to the apprehension of the child. Such a bolt arrangement for attachment creates safety issues since the bolts may become loose during transport. Further, the pole is located on one side of the wagon between the front and rear wheels making that side essentially inaccessible for entry and exit and for tending to the passenger. Further, by being located near the rear of the wagon, the I.V. device is positioned over the upper body of the child when the child is riding face forward. Should the I.V. become loose and fall, a major injury may be incurred by the child. With a bolt on attachment of the I.V. pole, should it become loose and free of attachment to the wagon (or wheel chair) there is a risk that the I.V. catheters will be pulled out of the child causing great pain and excessive bleeding. The wagon of the '094 patent is a single pivot front axle type wagon. During sharp turns, such wagons can be unstable since the front support points (front wheels) move toward the center of gravity of the wagon narrowing the front wheel support width. When the front wheels are in a sharp turn position, the wagon is also unstable at rest increasing the probability it will tip and thereby create more apprehension in the child being transported.

Another wagon of the above general type has an I.V. pole permanently mounted to the wagon on the rear end and outboard of the perimeter of the wagon bed and wheels. By being rear mounted, the center of gravity of the wagon and attachments is more rearward on the wagon. When a pulling force is applied to the wagon's handle, the front of the wagon has a tendency to lift more because of additional weight of the pole and whatever device is attached thereto creating apprehension in the passenger as well as raising safety concerns. Also, by being rear mounted, the I.V. device is positioned above the upper body of a forward facing child presenting the safety concerns discussed above.

Although the above discussion was directed to I.V. devices, it is pointed out that other medical devices may also need to be moved with the child compounding the problems discussed in reference to I.V. devices. Such devices include portable gas supplies like oxygen tanks and tube feeders for liquid diet foods.

It is believed important for safety, effective treatment and comfort of a child, that their apprehension be kept as low as possible. The elimination unhappiness and of sources of potential apprehension is thus important. As discussed above, sources of unhappiness and apprehension include immobility, the type of vehicle used for transport, the inability to quickly and easily ready the child and I.V. for transport and departure from the vehicle and the stability of the vehicle. Whether a staff member or a family member is using the wheelchair or wagon for transport, the problems encountered are generally the same.

SUMMARY OF THE INVENTION

Among the several objects and features of the present invention may be noted the provision of a transport device that will create an atmosphere of fun when used by a child; the provision of such a device that is easy and quick to attach an I.V. pole to; the provision of such a device that is easy and quick to remove an I.V. pole from; the provision of such a device that provides room on both sides of the device for assisting the entry and exit of a child; the provision of such a device that is stable in operation and at rest; the provision of such a device that is stable during movement and when at rest regardless of the positions of its guiding wheels; the provision of such a device that is safe and convenient for child and medical device transport; and the provision of such a device that is economical to manufacture.

The present invention involves the provision of a wagon for transporting a person in a medical care facility. The wagon includes a wagon body having an upwardly facing support surface and an upstanding guardrail extending around a substantial portion of the support surface. The body has a front end and a rear end and opposite sides forming a wagon body perimeter. A handle is connected to the wagon body at the front end for applying a pulling force to the wagon body. Wheels are rotatably mounted on the body with a pair of the wheels positioned adjacent the front end and a pair of the wheels positioned adjacent the rear end with a substantial portion of the support surface being positioned between outermost portions of the front and rear wheels. The wagon body, guardrail, handle and wheels form a wagon. A pole with a top end and a bottom end is provided.

A pole mount is secured to the wagon and is adapted for mounting the pole on the wagon. The wagon provides substantially the entirety of support for the pole. The pole mount is positioned inboard of said wagon body perimeter and the pole has a substantial portion thereof positioned inboard of the wagon body perimeter.

A further aspect of the present invention is the provision of a wagon for use in transporting children in a medical care facility who require equipment or intravenous fluid during transport. The wagon comprises a body sized and shaped for receiving a child, the body having a front end, a rear end, sides and a floor for supporting the child. Wheels are located generally at the front and rear ends of the body and mounted on the body for rolling support of the body on a surface. An elongate handle is connected to the body generally at the front end thereof and extending forwardly for pulling the wagon. A pole is supported by the wagon and has a support portion extending over the wagon floor. The support portion is adapted for mounting medical equipment and/or intravenous fluid containers thereon whereby the equipment and containers are disposed at least partially over the wagon floor to increase stability of the wagon when pulled along the surface by the handle.

Other objects and features will be in part apparent and in part pointed out hereinafter.

BRIEF DESCRIPTION OF THE DRAWINGS

FIG. 2 is an enlarged fragmentary perspective of a right front corner of the wagon showing a mount for an I.V. pole;

FIG. 3 is an enlarged section taken along the line 3—3 in, FIG. 2 and shows a lower portion of an I.V. pole;

FIG. 5 is an enlarged fragmentary perspective of the right front corner of the wagon viewed from the interior of the wagon.

Corresponding reference characters indicate corresponding parts throughout the several views of the drawings.

DETAILED DESCRIPTION

Figure 1:
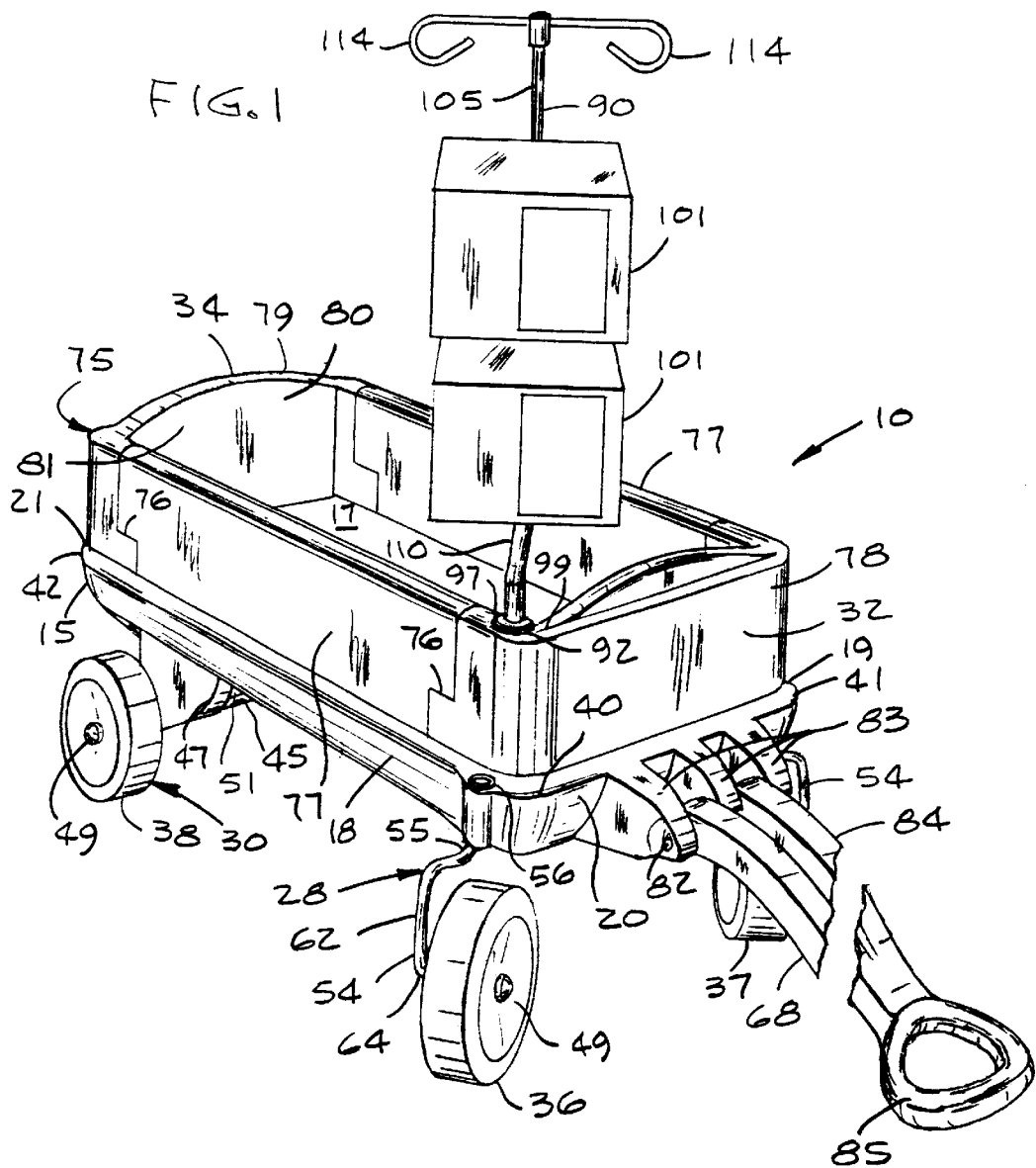
FIG. 1 is a perspective of a wagon for use in transporting a child in a medical care facility.

As seen in FIG. 1, a transport device is provided which is preferably in the form of a wagon designated generally by the numeral 10. The wagon 10 includes a bed 15 which has an upwardly facing child support surface (or "floor") 17. The bed 15 includes opposite side edges 18, 19, a front end edge 20 and rear end edge 21. The edges 18–21 form an outer perimeter for the bed 15. The bed 15 also includes a downwardly facing bottom panel 25 forming a portion of an undercarriage 26 (FIG. 4).

Figure 4:
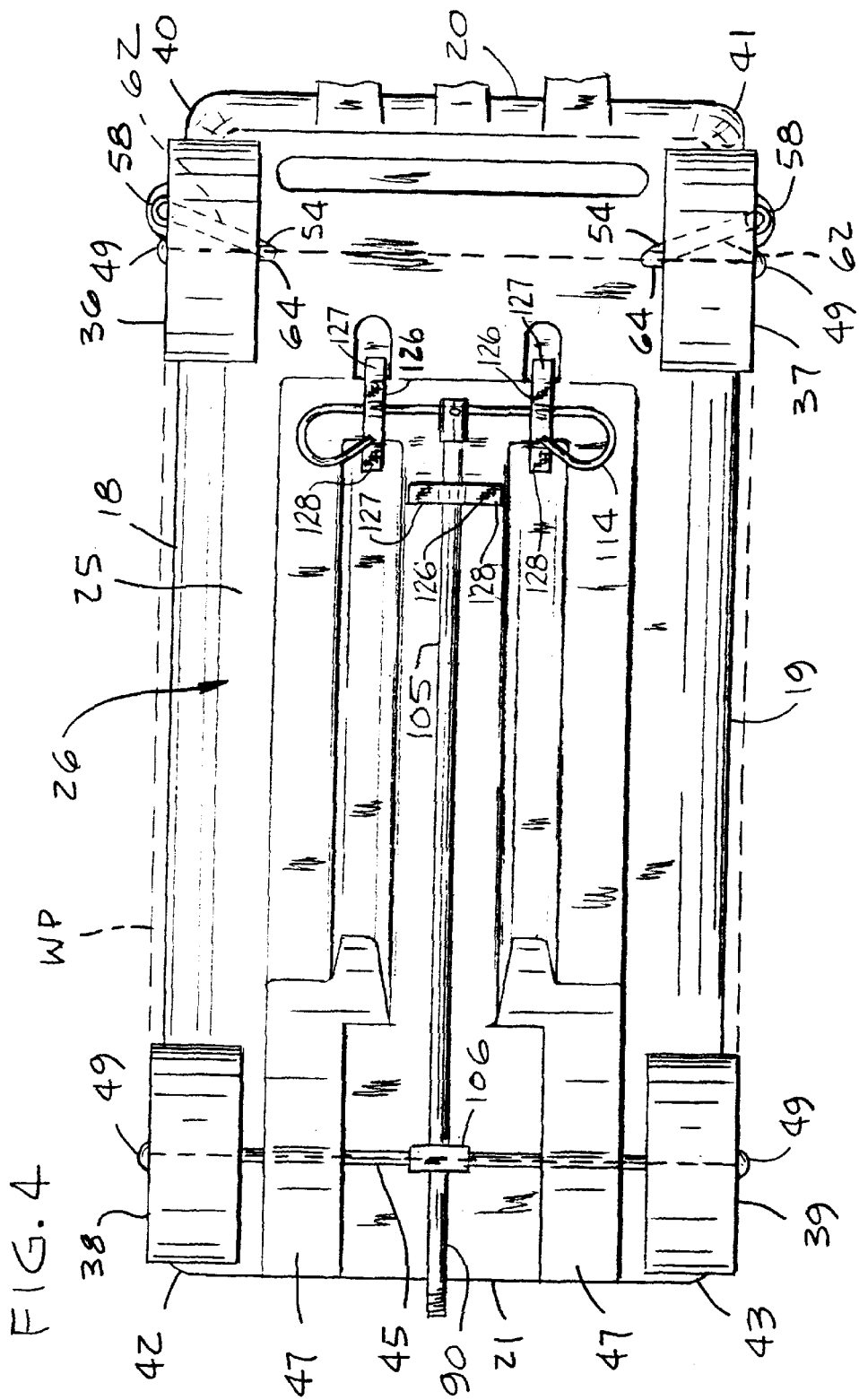
FIG. 4 is a bottom of the wagon showing the I.V. pole in a stowed position.

The wagon 10 is provided with front and rear wheel arrangements 28, 30 adjacent the front 32 and rear 34 of the wagon 10 respectively (see FIGS. 1 and 4). Preferably, the front wheel arrangement 28 includes two wheels 36, 37 and the rear wheel arrangement 30 also includes two wheels 38, 39. The wheels 36, 37 are spaced apart across the width of the wagon 10 with each being positioned adjacent a respective front corner 40, 41 of the wagon. The wheels 38, 39 are spaced apart across the width of the wagon 10 with each being positioned adjacent a respective rear corner 42, 43 of the wagon. The rear wheels 38, 39 are rotatably mounted on an axle 45 that is secured to the wagon 10 via brackets 47 depending from the bottom panel 25. Preferably, the brackets 47 are integral with the bed 15 and are laterally spaced apart. The wheels 38, 39 are mounted to the axle 45 by press nuts 49. The brackets 47, bottom surface 25 and the axle 45 define an opening 51 therebetween.

The front wheels 36, 37 are mounted to the wagon 10 preferably for independent pivoting movement whereby they individually pivot about offset vertical axes and remain adjacent their respective corner 40, 41 even during sharp turns. As shown in FIGS. 1 and 4, the front wheels 36, 37 are each rotatably mounted on its own axle bracket 54. The axle brackets 54 are of the self pivoting type, i.e., they turn when a force is applied to the wagon 10 similar to the operation of the front wheels on a grocery cart. As shown, the axle bracket 54 includes a generally vertical pivot pin 55 pivotally mounted to the bed 15 and retained in a bearing 56 via a support shoulder 58 and a swaged head 60. An arm 62 extends from the pivot pin 55 to an axle 64. Preferably the pivot pin 55, arm 62 and axle 64 are an integral structure formed from a metal rod. The arm 62 depends from the pivot pin 55 and inclines downwardly and backwardly from the pivot pin 55 whereby the axle 64 is behind or in a trailing position relative to the pivot pin 55 (and also relative to the direction of wagon movement). When the wagon 10 moves in response to a motive force such as by pulling a tongue or handle 68, the axle 64 will assume the trailing position and be generally perpendicular to the pulling force. The front wheels 36, 37 will follow but, unlike the wagons using a single front axle with a center pivot, remain adjacent their respective front corner 40, 41 to maintain the wagon 10 stable during movement and at rest regardless of front wheel orientation.

The wheels 36–39 form a wagon 10 support perimeter WP that remains substantially the same regardless of the pivotal orientation of the front wheels 36, 37. The wheel support perimeter WP is defined by the outermost ground contact areas of the wheels 36–39 (as shown by the dashed lines of FIG. 4). Further, at least a majority of the bed 15, both laterally and transversely, is inboard of the wheel support perimeter.

The wagon 10 is provided with a guardrail or rack designated generally as 75 (see FIG. 1). The guardrail 75 comprises a pair of side rails 77, a front rail 78 and a rear rail 79. The guardrail 75 can be partly or totally removably mounted on the bed 15 or can be permanently attached to the bed. Preferably, the rails 77–79 are separate parts from the bed 15 for facilitating manufacture of the wagon 10. After manufacture of the various parts, they are assembled to form the wagon. The rails 77–79 have posts (not shown) that fit into sockets (not shown) in the bed 15 for mounting the rails to the bed. The side rails 77 may additionally be mounted to the front and rear rails 78, 79 by posts (not shown) in sockets (not shown) as at the junctions 76. The guardrail 75 is upstanding and substantially completely surrounds the bed 15 and is inboard of the bed perimeter and preferably the side or longitudinal portions of the wheel perimeter WP. Alternatively, the side rails 77 could be hingedly mounted to the bed 15 such that they could be dropped down, without removal, to facilitate entry into and exit from the wagon 10. The guard rail 75 and bed 15 form a passenger compartment 80 with an upwardly opening top 81.

The wagon 10 is provided with the handle 68. The handle 68 is pivotally attached to the front of the wagon 10 by a pivot pin 82 extending thru hitch brackets 83. The handle 68 includes a shank 84 extending from the pivot pin 82 terminating in a D-shaped grip 85. The grip 85 is adapted to be grasped by a person to provide motive force to the wagon 10. Preferably, the pivot pin 82 permits movement of the handle 68 about a generally horizontal axis and in a generally vertical plane. The handle 68 will not pivot substantially laterally relative to the bed 15. To effect steering of the wagon 10, a lateral or sideways force is applied to the handle 68.

It is preferred that the bed 15, guard rail 75, handle 68 and wheels 36–39 be made of polymeric material. The use of polymeric material facilitates cleaning and disinfecting. Preferably these components are of molded construction, e.g., by rotational molding, leaving a hollow core for weight and material reduction while maintaining strength. A preferred wagon is a Trail Blazer model 2200 available from Radio Flyer, Inc. of Chicago, Ill. The wagon 10 is adapted for mounting an I.V. pole 90 to the wagon 10 (see FIGS. 2, 3 and 5). Preferably, the pole 90 is removably mounted to the wagon 10. As best seen in FIGS. 2 and 3, a socket (broadly "mount") 92 is secured to the guard rail 75 at a front corner 40 of the wagon 10. Preferably, the socket 92 extends through a generally vertical bore 93 in the front rail 78 and a second generally vertical through hole 94 thru the bed 15. The socket 92 is positioned between walls 96A, 96B and the outside surfaces 96C, 96D of the front rail 78. A fastener 95, such as a hex nut is secured to the bottom end of the socket 92. The upper end of the socket 92 has a laterally extending flange 97 engaged with a top surface 99 of the front rail 78. The socket 92 captures the front rail 78 and bed 15 between the fastener 95 and flange 97 for securement to the wagon 10. The socket 92 includes a thru bore 100 with a generally vertically oriented longitudinal axis.

The pole 90 with opposite lower and upper ends 104, 105 is provided for supporting a medical device, e.g., a liquid storage and injection device such as an infusion pump 101 (FIG. 1) or I.V. The lower end 104 is received in the bore 100 of the socket 92. A stop collar 106 (see FIG. 5) is secured to the pole 90 adjacent the lower end 104 and engages the flange 97 to limit the axial movement of the pole into the bore 100 and to provide vertical support for the pole. A generally L-shaped finger 108 extends outwardly and then downwardly from the collar 106 forming a channel 109 between the finger and the pole. A portion of the front rail 78 is received in the channel 109 and thereby prevents rotation of the pole 90 in the socket 92 and fixes the rotational position of the pole 90.

The pole 90 is mounted in a manner to not destabilize the wagon 10 and to provide easy entry into and exit from the wagon. Further, the wagon 10 substantially entirely supports and in the illustrated embodiment, entirely supports the pole 90 and devices mounted thereon. As seen in FIGS. 1 and 5, a substantial portion of the pole 90 is inboard of the outside perimeter of the bed 15 and the side or longitudinal portions of the wheel perimeter WP and is positioned above the bed 15. The pole 90 is bent at 110 adjacent the lower end 104 and above the collar 106. The orientation of the finger 108 relative to the bend 110 is such that the upper portion 105 of the pole 90 is positioned inboard of the guard rail 75 and the wheels 36–39 thus positioning the center of gravity of the pole and the I..V. bag when connected to a hook 114 secured to the upper end 105 also inboard of the bed perimeter, guardrail 75 and the wheel perimeter. Any medical device, such as an infusion pump, gas supply, tube feeder, etc., mounted on the pole will also be over the wagon bed inboard of the bed perimeter, guardrail 75 and the wheel perimeter. Such devices will also be positioned over the lower body portion of the child and not over the upper body portion of the child when positioned in a forwardly facing orientation. If an I.V. drip type bag is used, it will be out of easy reach of the child reducing the chance of tampering. The pole 90 and medical device are easily mounted on the wagon 10 and are easily removed from the wagon when it and the transported child reach their destination. Only one staff member is required to move the wagon, attached medical device(s) and patient thru the facility.

The wagon 10 is able to stow the pole 90 on the wagon when the pole is not in use. Preferably, the pole is stowed in a position that will not present itself as a danger to personnel and equipment during moving and storage of the wagon 10 and its length is such that a substantial portion and preferably its entirety is within the wagon bed perimeter. As seen in FIG. 4, the pole 90 is removably mounted to the undercarriage of the wagon 10. The lower end 104 of the pole 90 is received over the axle 45 with the axle being positioned within the channel 109 formed by L-shaped finger 108 and the pole. The lower end 104 is thus removably retained on the rear axle 45. Means is also provided on the underside of the wagon 10 to releasably retain the upper end 105 of the pole 90. The retention means includes a spring action clip 126 which may be made of stainless steel. The clip 126 utilized two arcuate fingers 127, 128 forming a pole receiving area (not shown) approximately equal to the diameter of the pole 90. The opening 129 adjacent the free ends of and between the fingers is smaller than the diameter of the pole 90 whereby the pole is releasably retained between the fingers of the clip 126. The clip 126 is secured to the bottom panel 25 of the undercarriage of the wagon 10. The pole 90 is stowed for carriage by forcing the pole between the fingers into the enlarged area between the fingers and released from its stowed position under the wagon by simply pulling the pole out from between the fingers.

The above described wagon 10 is well adapted for use in a medical facility for transporting children to make moving about more fun and thereby reduce apprehension. The wagon requires only one staff member to operate. It also allows for easy entry into and exit from thereby making the trip more enjoyable and also less apprehensive. The pole 90 and its mount also provide for the easy mounting and removal of medical devices and can be conveniently stowed under the wagon out of the way when not in use. The wagon is also stable in operation because of the front wheel configuration and the mounting of the pole.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense.

What is claimed is:

1. A wagon for transporting a person in a medical care facility comprising:
    a wagon body having an upwardly facing support surface adapted to receive and support the person thereon and an upstanding guardrail extending around a substantial portion of the support surface, said body having a front end and a rear end and opposite sides forming a wagon body perimeter, said guardrail being of molded plastic with inner and outer walls defining a hollow interior;
    a handle connected to said wagon body at the front end for applying a pulling force to the wagon body;
    wheels rotatably mounted on said body with a pair of the wheels positioned adjacent the front end and a pair of the wheels positioned adjacent the rear end with a substantial portion of the support surface being positioned between outermost portions of the front and rear wheels;
    a pole with a top end and a bottom end; and
    a pole mount secured to said wagon and adapted for mounting said pole on said wagon, said wagon providing substantially the entirety of support for said pole, said pole mount being positioned inboard of said wagon body perimeter and including a socket mounted to the guardrail and positioned between said inner and outer walls of said guardrail, said socket being mounted adjacent the front end of said wagon body and having a generally vertical passage for receiving the bottom end of said pole therein, said pole having a substantial portion thereof positioned inboard of said wagon body perimeter.

2. A wagon as set forth in claim 1 wherein said front wheels are each mounted on a respective pivot and thereby are separately pivotable for steering.

3. A wagon as set forth in claim 2 wherein each said wheel has an outermost point of contact with the ground, said contact points forming a wheel perimeter and said pole includes a bend therein positioning an upper portion of the pole inboard of the wheel perimeter.

4. A wagon as set forth in claim 1 wherein said pole includes a hook adjacent the top end and adapted for attaching an I.V. bag to the pole.

5. A wagon as set forth in claim 1 wherein said socket is located adjacent a front corner on one side of said wagon body.

6. A wagon as set forth in claim 5 wherein said guardrail includes a side rail on each side of said wagon body and said socket is positioned forward of the side rails.

7. A wagon as set forth in claim 1 including a finger secured to said pole with a portion spaced from the pole forming a channel therebetween, said channel receiving a portion of said guardrail therein to inhibit rotation of said pole when mounted in said socket.

8. A wagon as set forth in claim 1 wherein said pole includes a bend therein for positioning an upper portion of the pole inboard of said guardrail.

9. A wagon as set forth in claim 1 wherein said body includes a bottom surface and said wagon further includes means for releasably stowing said pole under said body for carriage.

10. A wagon as set forth in claim 1 wherein at least a central portion of the support surface is free of said pole mount and said pole for receiving the person onto the support surface.

11. A wagon for use in transporting children in a medical care facility who require equipment or intravenous fluid during transport, the wagon comprising a body sized and shaped for receiving a child, the body having a front end, a rear end, sides and a floor for supporting the child, wheels located generally at the front and rear ends of said body and mounted on the body for rolling support of the body on a surface, an elongate handle connected to the body generally at the front end thereof and extending forwardly for pulling the wagon, a pole releasably mounted on the wagon body and supported completely by the wagon, said pole having a bend therein curving towards locations above the wagon floor and a support portion extending over the wagon floor, said support portion being adapted for mounting medical equipment and/or intravenous fluid containers thereon whereby the equipment and containers are disposed at least partially over the wagon floor to increase stability of the wagon when pulled along the surface by the handle, and a mount sleeve disposed in the wagon body and adapted to receive an end of the pole therein.

12. A wagon as set forth in claim 11 wherein the pole is supported by the wagon body at the front end thereof.

13. A wagon for use in transporting children in a medical care facility who require equipment or intravenous fluid during transport, the wagon comprising a body sized and shaped for receiving a child, the body having a front end, a rear end, sides and a floor for supporting the child, wheels located generally at the front and rear ends of the body and mounted on the body for rolling support of the body on a surface, an elongate handle connected to the body generally at the front end thereof and extending forwardly for pulling the wagon, and a pole supported by the wagon and having a support portion extending over the wagon floor, said support portion being adapted for mounting medical equipment and/or intravenous fluid containers thereon whereby the equipment and containers are disposed at least partially over the wagon floor to increase stability of the wagon when pulled along the surface by the handle, and wherein the wagon further comprises a mount sleeve disposed in the wagon body and adapted to receive an end of the pole therein.

14. A wagon for transporting a person in a medical care facility comprising:

a wagon body having an upwardly facing support surface and an upstanding guardrail extending around a substantial portion of the support surface, said body having a front end and a rear end and opposite sides forming a wagon body perimeter;

a handle connected to said wagon body at the front end for applying a pulling force to the wagon body;

wheels rotatably mounted on said body with a pair of the wheels positioned adjacent the front end and a pair of the wheels positioned adjacent the rear end with a substantial portion of the support surface being positioned between outermost portions of the front and rear wheels, said wagon body, guardrail, handle and wheels forming a wagon;

a pole with a top end and a bottom end;

a pole mount secured to said wagon and adapted for mounting said pole on said wagon, said wagon providing substantially the entirety of support for said pole, said pole mount being positioned inboard of said wagon body perimeter, said pole having a substantial portion thereof positioned inboard of said wagon body perimeter;

said wagon body including a bottom surface and said wagon further includes a fastener to releasably stow said pole under said body for carriage when not in use.

15. A wagon for transporting a person in a medical care facility comprising:

a wagon body having an upwardly facing support surface adapted to receive and support the person thereon and an upstanding guardrail extending around a substantial portion of the support surface, said body including a bottom surface and having a front end and a rear end and opposite sides forming a wagon body perimeter;

a handle connected to said wagon body at the front end for applying a pulling force to the wagon body;

wheels rotatably mounted on said body with a pair of the wheels positioned adjacent the front end and a pair of the wheels positioned adjacent the rear end with a substantial portion of the support surface being positioned between outermost portions of the front and rear wheels;

a pole with a top end and a bottom end and having a substantial portion thereof positioned inboard of said wagon body perimeter;

a pole mount secured to said wagon and adapted for mounting said pole on said wagon, said wagon providing substantially the entirety of support for said pole, said pole mount being positioned inboard of said wagon body perimeter and including a socket mounted to the guardrail, said socket having a generally vertical bore for receiving the bottom end of said pole therein; and means for releasably stowing said pole under said body for carriage.

* * * * *